United States Patent
Sandusky et al.

(10) Patent No.: US 9,594,012 B1
(45) Date of Patent: Mar. 14, 2017

(54) SLIDING FRICTION TESTER FOR EXPLOSIVE MATERIAL

(71) Applicants: Harold W. Sandusky, Fulton, MD (US); Joshua E. Felts, Indian Head, MD (US)

(72) Inventors: Harold W. Sandusky, Fulton, MD (US); Joshua E. Felts, Indian Head, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 79 days.

(21) Appl. No.: 14/545,326

(22) Filed: Apr. 23, 2015

(51) Int. Cl.
| | |
|---|---|
| *G01N 19/02* | (2006.01) |
| *G01N 33/22* | (2006.01) |
| *G01N 19/00* | (2006.01) |

(52) U.S. Cl.
CPC .............. *G01N 19/02* (2013.01); *G01N 19/00* (2013.01); *G01N 33/22* (2013.01); *G01N 33/227* (2013.01)

(58) Field of Classification Search
CPC ........ G01N 19/00; G01N 19/02; G01N 33/22; G01N 33/227
See application file for complete search history.

(56) References Cited

U.S. PATENT DOCUMENTS

| | | | |
|---|---|---|---|
| 3,535,911 A | * | 10/1970 | Armstrong ............. G01N 19/02 73/9 |
| 5,107,448 A | | 4/1992 | Nash |
| 5,490,410 A | | 2/1996 | Markstrom |
| 5,900,531 A | | 5/1999 | Mani et al. |
| 6,094,967 A | | 8/2000 | Cavdar |
| 6,199,424 B1 | | 3/2001 | Mani et al. |
| 6,349,587 B1 | | 2/2002 | Mani et al. |
| 6,446,486 B1 | | 9/2002 | deBoer et al. |

FOREIGN PATENT DOCUMENTS

| | | | |
|---|---|---|---|
| CN | 101216478 A | * | 7/2008 |
| CN | 104237117 A | * | 12/2014 |

(Continued)

OTHER PUBLICATIONS

Akst, I.B., Two New Methods for Determining Frictional Sensitivity of Explosives, Annals of the New York Academy of Sciences, vol. 152, Issue 1, Dec. 16, 2006.*

(Continued)

*Primary Examiner* — David Bolduc
(74) *Attorney, Agent, or Firm* — Fredric Zimmerman

(57) ABSTRACT

A friction tester for explosive material includes a cylinder with a piston disposed therein for sliding movement along the cylinder's axial dimension. The piston includes first and second opposing faces. A plate is coupled to the piston and extends away from the first face thereof along the cylinder's axial dimension. The plate includes a portion extending from the cylinder. The plate has opposing surfaces of defined surface roughness. A sample holder disposed adjacent to the cylinder holds an explosive material sample against each of the opposing surfaces of the plate at the portion thereof that extends from the cylinder. A driver coupled to the second face of the piston drives the piston in the cylinder's axial dimension such that the plate moves relative to and against each explosive material sample.

22 Claims, 2 Drawing Sheets

(56) References Cited

FOREIGN PATENT DOCUMENTS

CN            104266962 A   *   1/2015
CN            104267169 A   *   1/2015

OTHER PUBLICATIONS

Brown, John A., A Study of Friction Fundamentals in Explosives, Dec. 1970.*

Durand, B., Delvare, F., Bailly, P. et al. Friction Between Steel and a Confined Inert Material Representative of Explosives Under Severe Loadings, Exp Mech (2014) 54, p. 1293-1303, May 24, 2014.*

* cited by examiner

SLIDING FRICTION TESTER FOR EXPLOSIVE MATERIAL

ORIGIN OF THE INVENTION

The invention described herein was made in the performance of official duties by employees of the Department of the Navy and may be manufactured, used, licensed by or for the Government for any governmental purpose without payment of any royalties thereon.

FIELD OF THE INVENTION

The invention relates generally to friction testing, and more particularly to a friction testing apparatus for testing sliding fiction effects on explosive materials.

BACKGROUND OF THE INVENTION

Small-scale friction testing of explosive materials typically involves the pinching of a small explosive material sample between two hard surfaces. However, there are other scenarios where the explosive material will experience a sliding motion across a surface with no pinching thereof such as when a container filled with explosive material impacts a hard surface to thereby cause the explosive material to compress and move towards the impacted hard surface. For example, a warhead's explosive fill is compressed within the warhead's container and slides relative to the container wall when the warhead experiences sudden acceleration as is the case during a warhead penetration event. Friction occurs between the explosive and container wall or its lining, or possibly within the explosive if the explosive adheres to the container or its liner. It is important to understand how sliding friction could cause unintended reaction of the explosive for various handling and operational scenarios.

SUMMARY OF THE INVENTION

Accordingly, it is an object of the present invention to provide a friction tester for explosive materials.

Another object of the present invention is to prove a laboratory scale device for testing sliding friction that would be experienced by explosive materials sliding along a warhead's inner walls.

Other objects and advantages of the present invention will become more obvious hereinafter in the specification and drawings.

In accordance with the present invention, a friction tester for explosive material includes a cylinder having an axial dimension. A piston is disposed in the cylinder for sliding movement therein along its axial dimension. The piston includes a first face and a second face opposing the first face. A plate is coupled to the piston and extends away from the first face thereof along the axial dimension of the cylinder. The plate has a portion thereof extending from the cylinder. The plate has opposing surfaces of defined surface roughness. A sample holder is disposed adjacent to the cylinder to hold an explosive material sample against each of the opposing surfaces of the plate at the portion thereof that extends from the cylinder. A driver is coupled to the second face of the piston for driving the piston in the cylinder's axial dimension where the plate experiences movement in a first direction such that the plate moves relative to and against each explosive material sample.

BRIEF DESCRIPTION OF THE DRAWINGS

Other objects, features and advantages of the present invention will become apparent upon reference to the following description of the exemplary embodiments and to the drawings, where corresponding reference characters indicate corresponding parts throughout the several views of the drawings and wherein.

DETAILED DESCRIPTION OF THE INVENTION

Figure 1:
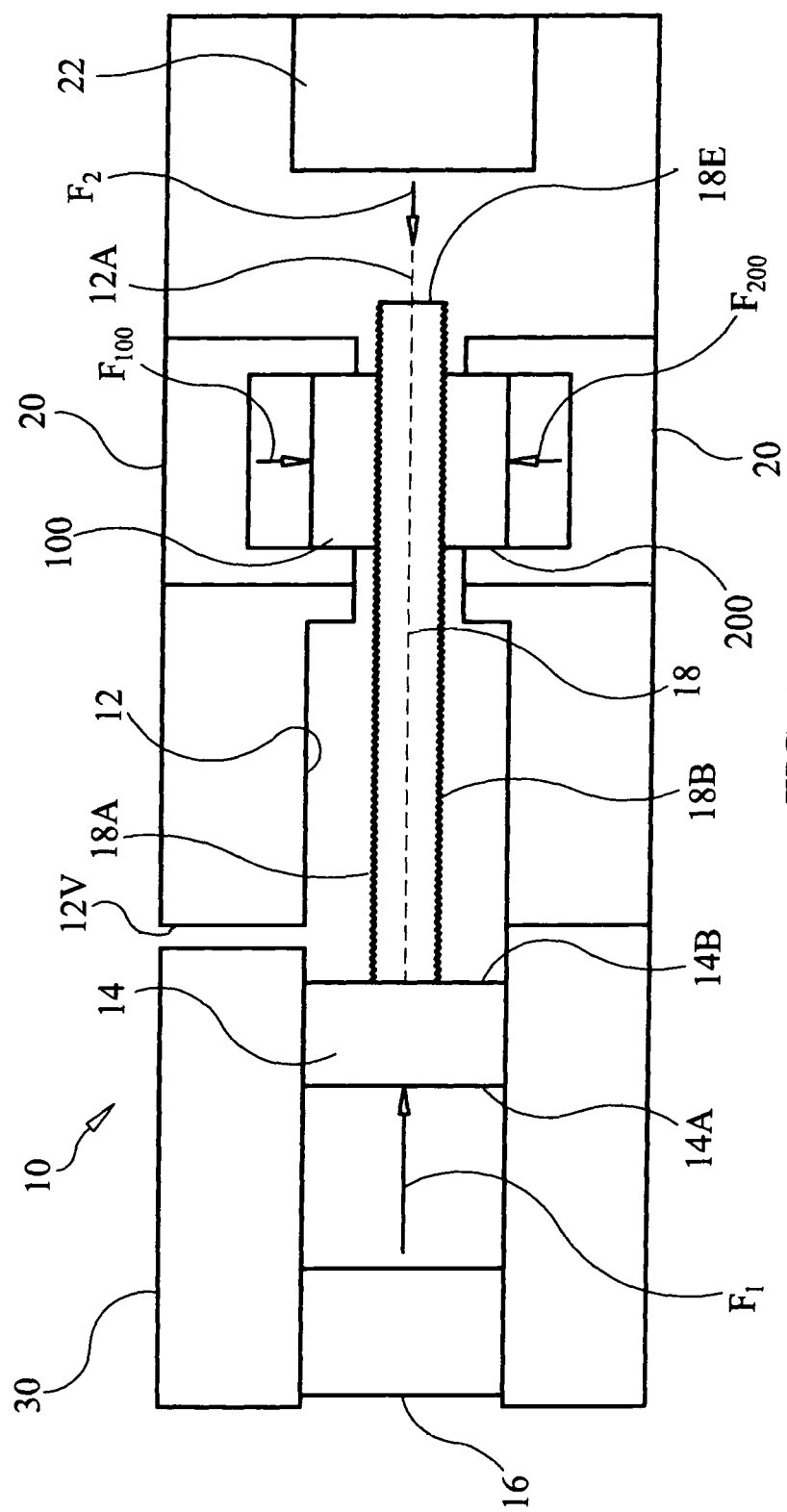
FIG. 1 is a side schematic view of a friction tester for explosive material in accordance with an embodiment of the present invention.

Referring now to the drawings and more particularly to FIG. 1, a schematic view of a friction tester for testing sliding friction experienced by explosive materials in accordance with an exemplary embodiment of the present invention is shown and is referenced generally by numeral 10. Friction tester 10 will be described for its use in evaluating siding friction that will be experienced by a warhead's explosive fill. Friction tester 10 may be constructed as a laboratory-scale device thereby greatly simplifying analysis of the acceleration and rebound sliding movement of a warhead's explosive fill.

Friction tester 10 includes a cylinder 12, a piston 14 disposed in cylinder 12 and capable of sliding back and forth axially in cylinder 12, a piston driver 16, a friction plate 18 coupled to piston 14, and a sample holder 20 disposed adjacent to cylinder 12. In some testing applications, an elastic bumper 22 may be provided. All of these elements may be contained/supported in a single housing 30, the design of which is not a limitation of the present invention.

Piston 14 forms a sliding fit within cylinder 12 such that piston 14 is limited to movement back and forth along the axial dimension of cylinder 12. The axial dimension of cylinder 12 lies along its longitudinal axis 12A. Piston 14 includes two opposing faces 14A and 14B disposed perpendicularly to longitudinal axis 12A.

Piston driver 16 is disposed adjacent to face 14A of piston 14. When activated, piston driver 16 applies a short-duration driving force $F_1$ to face 14A that moves piston 14 axially in cylinder 12. In an exemplary embodiment of the present invention, piston driver 16 is an explosive device such that activation thereof generates explosion gases that define driving force $F_1$.

Figure 2:
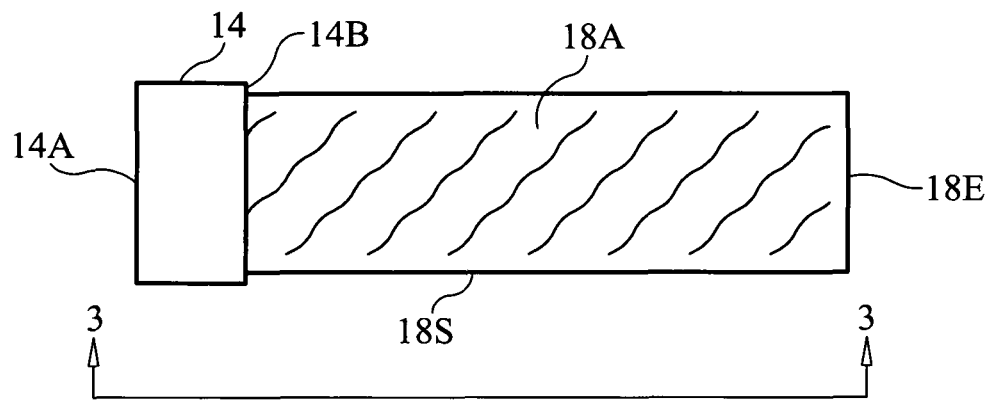
FIG. 2 is an isolated plan view of the friction tester's piston and plate.
Figure 3:
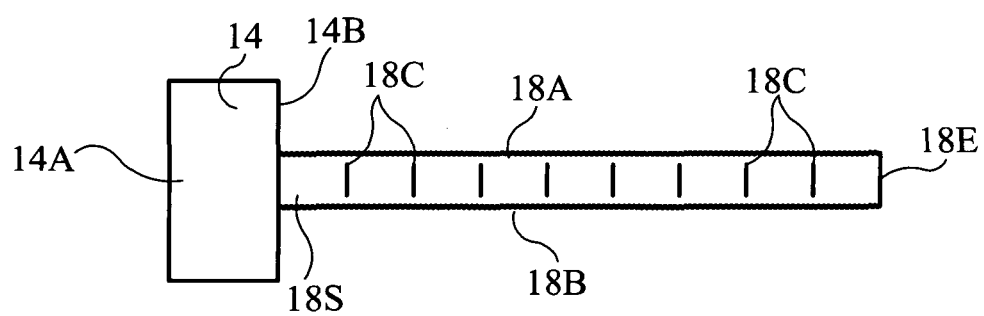
FIG. 3 is a side view of the piston and plate taken along line 3-3 in FIG. 2.

Referring additionally to FIGS. 2 and 3, friction plate 18 is a rigid plate coupled to face 14B of piston 14. Friction plate 18 extends along the axial dimension of cylinder 12, e.g., along longitudinal axis 12A. Friction plate 18 defines opposing surfaces 18A and 18B that are generally parallel to one another. In an exemplary embodiment of the present invention, each surface 18A and 18B is a generally planar surface that is or has been roughened to present a friction surface of interest. In the figures, surface roughness is illustrated by irregular wavy lines. When friction tester 10 is being used to evaluate sliding friction effects on a warhead's explosive fill, each of surfaces 18A and 18B may be roughened to mimic a warhead's container wall or liner that will interface with the warhead's explosive fill. Surfaces 18A and 18B may have the same, that is, substantially equal, or different, that is, non-equal, surface roughness without departing from the scope of the present invention.

Friction plate 18 includes a portion thereof that extends from cylinder 12 and through sample holder 20. In general, sample holder 20 positions and holds a sample 100 of explosive material against surface 18A extending from cylinder 12, and a sample 200 of explosive material against surface 18B extending from cylinder 12. Samples 100 and 200 may be the same or different explosive materials without departing from the scope of the present invention. More specifically, sample holder 20 applies holding force $F_{100}$ to sample 100 and, separately, a holding force $F_{200}$ to sample 200. Forces $F_{100}$ and $F_{200}$ are equal in magnitude and are applied towards one another in a direction that is perpendicular to longitudinal axis 12A of cylinder 12. Forces $F_{100}$ and $F_{200}$ should remain equal to each other throughout the testing process. The magnitude of forces $F_{100}$ and $F_{200}$ are selected to mimic the forces that samples 100/200 will experience when, for example, they are packed into a warhead and are in contact with the warhead's container wall/liner. Sample holder 20 may be a hydraulic-type of device such that forces $F_{100}$ and $F_{200}$ are hydraulic pressure forces.

A side 18S of friction plate 18 may include markings or indicia 18C used to track movement of plate 18. Such indicia 18C may be viewed through a window (not shown) provided in housing 30.

In operation, piston driver 16 is activated to apply a short-duration driving force $F_1$ to piston 14. As piston 14 moves axially in cylinder 12, surfaces 18A/18B slide past samples 100/200 thereby generating friction forces as surfaces 18A/18B are in pressurized contact with samples 100/200. Cylinder 12 may be provided with one or more vent ports 12V. Such venting is particularly important when driving force $F_1$ is created by explosion gases. In this case, venting of the explosion gases occurs after piston 14 passes/clears vent port 12V.

As mentioned above, a warhead's explosive fill experiences acceleration and rebound. The driving force $F_1$ provides the acceleration aspect experienced by an explosive fill. The rebound aspect may be provided by elastic bumper 22. More specifically, elastic bumper 22 is positioned in a spaced-apart relationship with the outboard end 18E of plate 18 where the spaced-apart relationship is defined prior to a friction test. During the above-described friction test, outboard 18E is driven to impact elastic bumper 22. Since driving force $F_1$ is of short duration and the explosion gases associated with driving force $F_1$ are vented via vent port 12V, elastic bumper 22 is able to apply a rebound force $F_2$ to outboard end 18E upon impact. Rebound force $F_2$ is directed in the axial dimension of cylinder 12 and in a direction that is opposite that of driving force $F_1$.

The advantages of the present invention are numerous. A laboratory-scale sliding friction tester is readily configured to mimic sliding acceleration-and-rebound friction forces that would be experienced by a warhead's explosive fill. The tester is readily adapted for testing a variety warheads/fills by changing the friction plate's surface roughness, the samples being tester, the acceleration/driving force $F_1$, the elastic bumper supplying the rebound force $F_2$ and/or sample holding forces $F_{100}/F_{200}$.

Although the invention has been described relative to a specific exemplary embodiment thereof, there are numerous variations and modifications that will be readily apparent to those skilled in the art in light of the above teachings. For example, one or more sensors may be coupled to the friction tester to sense/measure the various forces described herein to control the testing operation and/or collect measurement data. It is therefore to be understood that, within the scope of the appended claims, the invention may be practiced other than as specifically described.

Finally, any numerical parameters set forth in the specification and attached claims are approximations (for example, by using the term "about") that may vary depending upon the desired properties sought to be obtained by the present invention. At the very least, and not as an attempt to limit the application of the doctrine of equivalents to the scope of the claims, each numerical parameter should be at least construed in light of the number of significant digits and by applying ordinary rounding.

What is claimed as new and desired to be secured by Letters Patent of the United States is:

1. A friction tester for explosive material, comprising:
   a cylinder including an axial dimension;
   a piston being disposed in said cylinder for sliding movement therein along said axial dimension, said piston comprises a first face and a second face opposes said first face;
   a plate being coupled to said piston and extending away from said first face thereof along said axial dimension of said cylinder, said plate comprises a portion thereof to extend from said cylinder, said plate comprises opposing surfaces of defined surface roughness;
   a sample holder being disposed adjacent to said cylinder and being adapted for holding an explosive material sample against each of said opposing surfaces of said plate at said portion thereof extending from said cylinder; and
   a driver being coupled to said second face of said piston for driving said piston in said axial dimension of said cylinder,
      wherein said plate experiences a first movement in a first direction such that said plate moves relative to and against each explosive material sample.

2. The friction tester as in claim 1, wherein at least one edge of said plate includes indicia to provide a visual indication of how much said plate moves when said piston is driven by said driver.

3. The friction tester as in claim 1, wherein said sample holder applies a pressure force to each explosive material sample, and wherein said pressure force is perpendicular to said axial dimension of said cylinder.

4. The friction tester as in claim 3, wherein said sample holder keeps said pressure force constant when said piston is driven by said driver.

5. The friction tester as in claim 1, wherein said surface roughness is substantially equal on each of said opposing surfaces of said plate.

6. The friction tester as in claim 1, wherein said surface roughness is non-equal on each of said opposing surfaces of said plate.

7. The friction tester as in claim 1, wherein each of said opposing surfaces of said plate is planar.

8. The friction tester as in claim 1, further comprising an elastic bumper being aligned with said plate for changing said first movement thereof in said first direction to a second movement thereof in a second direction opposite to said first direction.

9. A friction tester for explosive material, comprising:
   a cylinder including an axial dimension, said cylinder comprises at least one vent port;
   a piston being disposed in said cylinder to one side of said at least one vent port for sliding movement in said cylinder along said axial dimension, said piston comprises a first face and a second face opposes said first face;

a plate being coupled to said piston and extending away from said first face thereof along said axial dimension of said cylinder, said plate comprises a portion thereof to extend from said cylinder, said plate includes opposing surfaces of defined surface roughness;

a sample holder being disposed adjacent to said cylinder and being adapted for holding an explosive material sample against each of said opposing surfaces of said plate at said portion thereof extending from said cylinder; and an explosive driver being disposed adjacent to said second face of said piston for generating explosion gases that drive said piston in said axial dimension of said cylinder past said at least one vent port, wherein said plate experiences a first movement in a first direction such that said plate moves relative to and against each explosive material sample, and wherein said explosion gases vent through said at least one vent port when said first face of said piston passes said at least one vent port.

10. The friction tester as in claim 9, wherein at least one edge of said plate includes indicia to provide a visual indication of how much said plate moves when said piston is driven by said explosion gases.

11. The friction tester as in claim 9, wherein said sample holder applies a pressure force to each explosive material sample, and wherein said pressure force is perpendicular to said axial dimension of said cylinder.

12. The friction tester as in claim 11, wherein said sample holder keeps said pressure force constant when said piston is driven by said explosion gases.

13. The friction tester as in claim 9, wherein said surface roughness is substantially equal on each of said opposing surfaces of said plate.

14. The friction tester as in claim 9, wherein said surface roughness is non-equal on each of said opposing surfaces of said plate.

15. The friction tester as in claim 9, wherein each of said opposing surfaces of said plate is planar.

16. The friction tester as in claim 9, further comprising an elastic bumper being aligned with said plate for changing said first movement thereof in said first direction to a second movement thereof in a second direction opposite to said first direction.

17. A friction tester for explosive material, comprising:

a cylinder including an axial dimension;

a piston being disposed in said cylinder for sliding movement therein along said axial dimension, said piston comprises a first face and a second face opposes said first face;

a plate being coupled to said piston and extending away from said first face thereof along said axial dimension of said cylinder, said plate includes a portion thereof extending from said cylinder, and said plate includes opposing planar surfaces of defined surface roughness;

a sample holder being disposed adjacent to said cylinder and being adapted for applying an equal amount of hydraulic pressure to an explosive material sample being positioned adjacent to each of said opposing planar surfaces of said plate at said portion thereof extending from said cylinder;

a driver being coupled to said second face of said piston for driving said piston in said axial dimension of said cylinder, wherein said plate experiences a first movement in a first direction such that said plate moves relative to and against each explosive material sample; and an elastic bumper being aligned with said plate for changing said first movement thereof in said first direction to a second movement thereof in a second direction opposite to said first direction.

18. The friction tester as in claim 17, wherein at least one edge of said plate includes indicia to provide a visual indication of how much said plate moves when said piston is driven by said driver.

19. The friction tester as in claim 17, wherein said hydraulic pressure is applied perpendicular to said axial dimension of said cylinder.

20. The friction tester as in claim 19, wherein said sample holder keeps said hydraulic pressure constant when said piston is driven by said driver.

21. The friction tester as in claim 17, wherein said surface roughness is substantially equal on each of said opposing planar surfaces of said plate.

22. The friction tester as in claim 17, wherein said surface roughness is non-equal on each of said opposing planar surfaces of said plate.

\* \* \* \* \*